United States Patent
De Ferra et al.

(10) Patent No.: US 10,407,515 B2
(45) Date of Patent: Sep. 10, 2019

(54) METHOD FOR THE QUALIFICATION OF PREPARATIONS OF PENTOSAN POLYSULFATE, RAW MATERIALS AND PRODUCTION PROCESSES THEREOF

(71) Applicant: CHEMI S.P.A., Cinisello Balsamo (IT)

(72) Inventors: Lorenzo De Ferra, Patrica (IT); Annamaria Naggi, Legnano (IT); Maurizio Zenoni, Patrica (IT); Barbara Pinto, Patrica (IT)

(73) Assignee: CHEMI S.P.A., Cinisello Balsamo (IT)

( * ) Notice: Subject to any disclaimer, the term of this patent is extended or adjusted under 35 U.S.C. 154(b) by 46 days.

(21) Appl. No.: 14/762,784

(22) PCT Filed: Jan. 23, 2014

(86) PCT No.: PCT/EP2014/051347
§ 371 (c)(1),
(2) Date: Jul. 22, 2015

(87) PCT Pub. No.: WO2014/114723
PCT Pub. Date: Jul. 31, 2014

(65) Prior Publication Data
US 2016/0002365 A1    Jan. 7, 2016

(30) Foreign Application Priority Data
Jan. 24, 2013 (IT) .............................. MI2013A0112

(51) Int. Cl.
C08B 37/00    (2006.01)
G01N 24/08    (2006.01)

(52) U.S. Cl.
CPC ........ *C08B 37/0057* (2013.01); *C08B 37/006* (2013.01); *G01N 24/088* (2013.01)

(58) Field of Classification Search
None
See application file for complete search history.

(56) References Cited

FOREIGN PATENT DOCUMENTS

| EP | 0184480 | 6/1986 |
| WO | WO2009087581 | 6/2009 |
| WO | WO2012101544 | 8/2012 |
| WO | WO2012114349 | 8/2012 |

OTHER PUBLICATIONS

Teleman, A. et al., Carbohydrate Research, 2000, "Characterization of acetylated 4-O-methylglucuronoxylan isolated from aspen employing 1H and 13C NMR spectroscopy", vol. 329, pp. 807-815.*
Pinto, P.C. et al., Carbohydrate Polymers, "Structure of hardwood glucuronoxylans: modifications and impact on pulp retention during wood kraft pulping", 2005, vol. 60, pp. 489-497 (Year: 2005).*
Ahrgren, et al., "Pyridinium substitution during the sulfation of polysaccharides in the presence of pyridine", Carbohydrate Polymers, Applied Science Publishers, Ltd, Barking, GB, vol. 16, No. 2, Jan. 1, 1991 pp. 211-214.
Teleman, et al., "Characterization of O-acetyl-(4-O-methylglucurono)xylan isolated from birch and beech", Carbohydrates Research, Pergamon, GB, vol. 337, No. 4, Feb. 1, 2002, pp. 373-377.
Taubner, et al., "Structure of the flexible amino-terminal domain of prion protein bound to a sulfated glycan", Journal of Molecular Biology, Academic Press, U.K., vol. 395, No. 3, Jan. 22, 2010, pp. 475-490.
Search Report and Written Opinion of PCT/EP2014/051347 dated Apr. 16, 2014.

* cited by examiner

*Primary Examiner* — Shaojia A Jiang
*Assistant Examiner* — Bahar Craigo
(74) *Attorney, Agent, or Firm* — Silvia Salvadori, P.C.; Silvia Salvadori

(57) ABSTRACT

A method for the qualification and selection of manufacturing processes, raw materials, intermediates and batch production of pentosan polysulfate based on the identification of acetylated monosaccharide units, including units of xylose substituted with 4-O-methyl-glucuronic which also lead the acetyl group, as structural characterizing units, is disclosed.

2 Claims, 3 Drawing Sheets

METHOD FOR THE QUALIFICATION OF PREPARATIONS OF PENTOSAN POLYSULFATE, RAW MATERIALS AND PRODUCTION PROCESSES THEREOF

This application is a U.S. National Stage of PCT/EP2014/051347 filed 23 Jan. 2014 which claims priority to and the benefit of Italian Application No. MI2013A000112 filed 24 Jan. 2013, the contents of which applications are incorporated herein by reference in their entirety.

The present invention relates to methods and products based on the identification of characterizing structural units of pentosan polysulfate and the corresponding xylan without sulfate groups, in particular to products obtained by a method of qualification and selection of production processes, raw materials, intermediates, production batchs of pentosan polysulfate based on the identification of said characterizing structural units.

STATE OF THE ART

Several pharmaceutical products (for example Elmiron®, CCRIS 8869, Fibrase®, Fibrezym®, HSDB 7294, Hoe/bay 946, NSC 626201, SP-54, Thrombocid®, PZ68, Hemoclar®, Fibrocid® and Tavan®) contain, as active ingredient, pentosan polysulfate, a polysaccharide which main skeleton is constituted by sequences of sulfated xylose units linked together through a glycosidic β-(1-4) bond.

Being obtained from xylanes extracted by high trees such as beech, ramifications of 4-O-methyl-glucuronic acid are present and distributed in a not necessarily regular manner.

The chemical structure of pentosan polysulfate reported in the technical and scientific literature corresponds to the following formula 1:

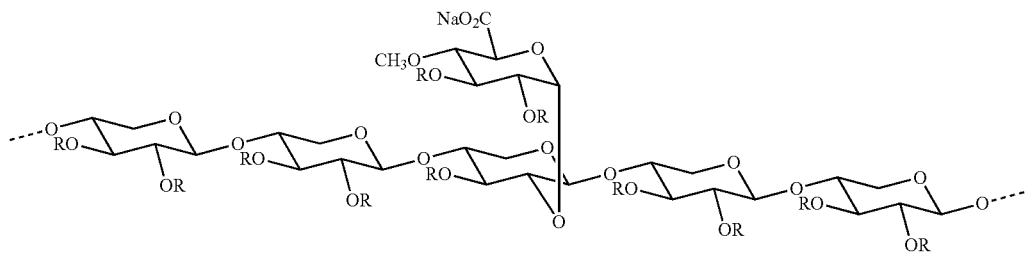

Formula 1 wherein R is H or SO$_3$Na.

The commercial product Elmiron® has a high sulfation degree and its molecular weight is 4000-6000 Dalton. Therefore pentosan polysulfate is made of a mixture of sulfated polysaccharides different each other for chain lengths and branching.

Pentosan polysulfate is used in the pharmaceutical field as anticoagulant and in the treatment of interstitial cystitis. It also shows several other biological activities including anti-tumor and anti-metastatic activity, antiviral and anti-inflammatory activity. It has been proposed as a therapeutic agent in the prevention and treatment of Prion Disease. It has effect in inhibiting the growth of the calcium oxalate crystals which lead to the formation of kidney stones. It also showed efficacy as anti-arthritic agent in animals suffering from osteoarthritis.

The polymerization degree and the structural variety can strongly influence the biological, immunological and toxicological activity of polysaccharides and of sulfated polysaccharides [T. Astrup Scand J Clin Lab Invest 137 (1952)]. A deep knowledge of the structural characteristics of pentosan polysulfate is therefore extremely important to ensure the therapeutic efficacy and safety of the pharmacological treatments which use it.

Because of the natural origin of the raw material and because of the processes of isolation and production, structural groupings which contribute to increase its structural complexity may be present on the polymer chain of xylan polysulfate. For example, in addition to sulfated xylose and sulfated 4-O-methyl-glucuronic acid, different monosaccharide units may be present.

Furthermore different sulfated and not sulfated polymeric species may be present, such as for example those deriving from other polysaccharides present in the natural source of the raw material.

In particular, the structural complexity of pentosan polysulfate may further increase depending on the method for the extraction of xylan from the natural source of the raw material. In fact such extraction method, depending from its selectivity, will provide xylan with different characteristics and different purity degrees. Moreover, during the transformation of xylan into the final product, it is possible that new impurities are introduced and that the transformation of those present or the introduction of new chemical groups in the polymer structure occur. These factors may also contribute to the complexity of the product as a whole.

Currently, the structural characterization of pentosan polysulfate has not been brought to the level of details required in view of the complexity of the product and therefore it is not suitable to the need of ensuring quality standard and equivalence of the production of the drugs on the market and to the proof of equivalence of generic pharmaceutical products.

A progress in the analytical characterization of pentosan polysulfate and in the identification of its characteristic structural units is therefore urgently needed. In the present context, characteristic structural unit means a part of the chemical structure of pentosan polysulfate or of xylan used for its preparation. Based on said characteristic structural unit various compositions or preparation methods of these polysaccharides can be qualified.

Qualification means the acknowledgement of the suitability of a polysaccharide composition or of a method for its preparation for the manufacturing of a pharmaceutical product for human use.

SUMMARY OF THE INVENTION

The invention is based on the discovery that the structure of pentosan polysulfate in the pharmaceutical products is characterized by the presence of some characteristic structural units that have not been so far identified in the chemical structure of formula 1 reported in the literature.

Such characteristic structural units have been identified by the Applicant and are acetylated monosaccharide units, and in particular units of acetylated xylose substituted with 4-O-methyl-glucuronic acid.

Therefore the present invention relates to methods for identifying the presence of said characteristic structural units in pentosan polysulfate and in xylan and to their application for the qualification of preparations of pentosan polysulfate, their raw materials such as xylan and their production processes.

A further object of the present invention is a method for the preparation of pentosan polysulfate and xylan comprising at least one qualification step based on said characteristic structural units.

DETAILED DESCRIPTION OF THE INVENTION

In a first aspect the present invention relates to polysaccharides of formula 2

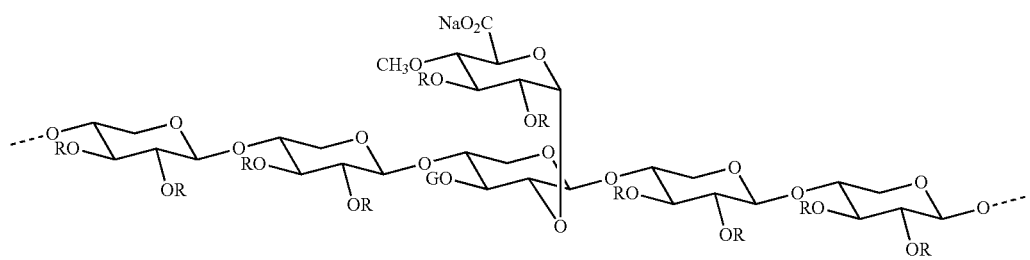

Formula 2 wherein
R is H or SO$_3$Na;
G is H, SO$_3$Na or acetyl;
obtained by a method comprising at least one identification or quantification step of acetylated monosaccharide units, and in particular units of acetylated xylose substituted with 4-O-methyl-glucuronic acid.

Pentosan polysulfate of formula 2 is characterized by the presence of xylose units substituted with 4-O-methyl-glucuronic acid and acetylated (G=acetyl) which represent characteristic structural units identified by the Applicant.

In a further aspect, the present invention relates to methods for identifying the presence of said characteristic structural units in pentosan polysulfate as well as in xylan and to their application for the qualification of preparations of pentosan polysulfate, their raw materials (xylans) and their production processes.

In a further embodiment, the present invention relates to the xylan of formula 2 wherein R is hydrogen and G is hydrogen or acetyl characterized by the presence of xylose units substituted with 4-O-methyl-glucuronic acid and acetylated (G=acetyl) which represent characteristic structural units identified by the Applicant.

The invention is based on the discovery that the structure of pentosan polysulfate present in pharmaceutical products is characterized by the presence of some characteristic structural units which may be correlated to the therapeutic efficacy and safety of pentosan polysulfate.

In the present context, the terms "pentosan polysulfate for pharmaceutical use", "pharmaceutical products containing pentosan polysulfate" and "commercial pentosan polysulfate" mean products on the market and/or known products which contain pentosan polysulfate as active ingredient for pharmaceutical use, with preferred reference to the medicinal product marketed under the name Elmiron®.

Figure 1:
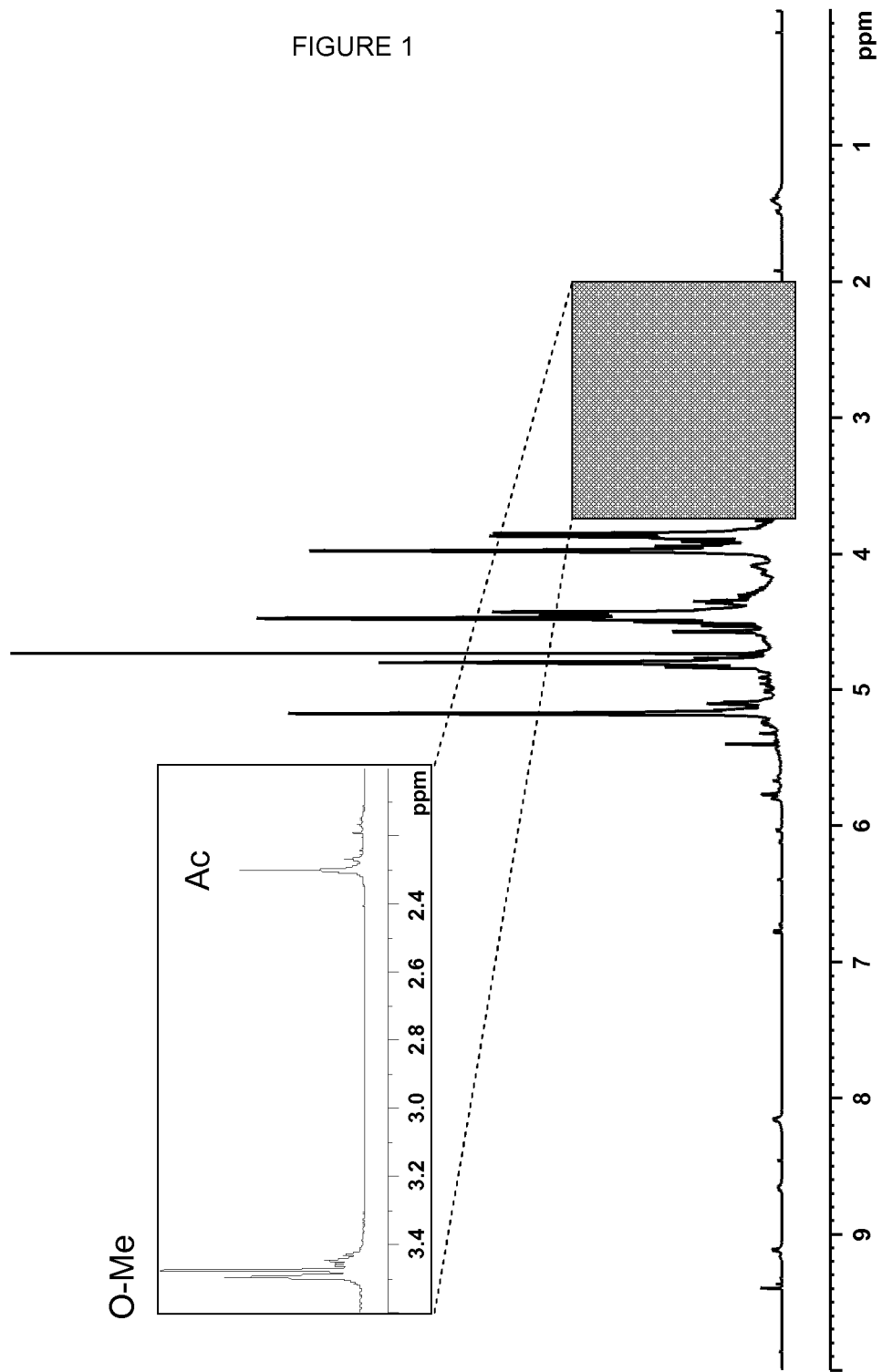
FIG. 1—$^1$H-NMR spectrum of pentosan polysulfate
FIG. 2—(A) HSQC NMR spectrum of pentosan polysulfate (XS) and (B) of xylan without sulfate groups obtained by desulfation of pentosan polysulfate (XSDS)
FIG. 3—Maldi TOF spectrum of xylan XSDS

By analyzing samples of commercial pentosan polysulfate by $^1$H-NMR spectroscopy, in particular Elmiron®, the signals corresponding to the polysulfate structure with high sulfation degree of formula 1 wherein the R groups are mainly sulfate groups have been detected, and furthermore it has been unexpectedly found that the spectrum shows the presence of signals at about 2.3 ppm corresponding to the presence of acetyl groups and the splitting of some peaks. In particular the splitting of the signal at about 3.48 ppm corresponding to the methoxy group of the 4-O-methyl-glucuronic acid units stands out (FIG. 1). Signals in the region 8.8-9.3 ppm due to pyridinium groups arising from the sulfation procedure used for the production of pentosan polysulfate for pharmaceutical use have been also detected.

The presence of pyridinium groups bound to pentosan polysulfate is reported in the literature, for example in WO03073106 and Carbohydrate Polymers 16 (1991) 211-214.

On the contrary, the splitting of the $^1$H-NMR signal relative to the methoxy group of the unit of 4-O-methyl-glucuronic acid and the presence of signals corresponding to acetyl groups are not expected on the basis of the chemical structure of pentosan polysulfate reported in the technical and scientific literature and represented by formula 1.

The Applicant has taken into consideration the possibility that the NMR signal at about 2.3 ppm was caused by traces of solvents or salts used in the production process of pentosan polysulfate and not completely removed during purification. Chemical analyses such as the determination of the free anions by HPLC, gas chromatographic analysis of residual solvents and comparison of the $^1$H-NMR chemical shifts in the 2.3 ppm region allowed to exclude the presence of species such as acetate ion and solvents such as acetic acid and ethyl acetate in such quantities to justify the presence of the $^1$H-NMR signal at about 2.3 ppm in the spectrum of pentosan polysulfate shown in FIG. 1.

Said $^1$H-NMR signal was then attributed to the presence of an acetyl group chemically bound to pentosan polysulfate.

The xylan from beech is used as a raw material in the manufacture of pharmaceutical products of pentosan polysulfate for human use.

The native xylan from beech is constituted by chains of beta 1-4 xylose partially acetylated at positions 2 and 3;

there are also units of alpha 4-O-methyl-glucuronic acid bound to position 2 of the xylose unit of the polysaccharide chain [see for example Carbohydrate Research 337 (2002) 373-377]. The processes commonly used for the isolation of xylan from beech involve the use of strongly alkaline solutions in which the xylan shows a quite good solubility; under these conditions the complete deacetylation of xylan occurs.

It is therefore surprising to have identified the presence of the acetyl function bound to pentosan polysulfate; in view of the potential implications on the biological and toxicological activities of pentosan polysulfate for pharmaceutical use, the acetyl group is a characterising structural units of the product.

For the structural identification of the unit characterizing pentosan polysulfate, experiments based on NMR spectroscopy were carried out exploiting the potential of this technique in the structural analysis of polysaccharides and sulfated polysaccharides.

Figure 2:
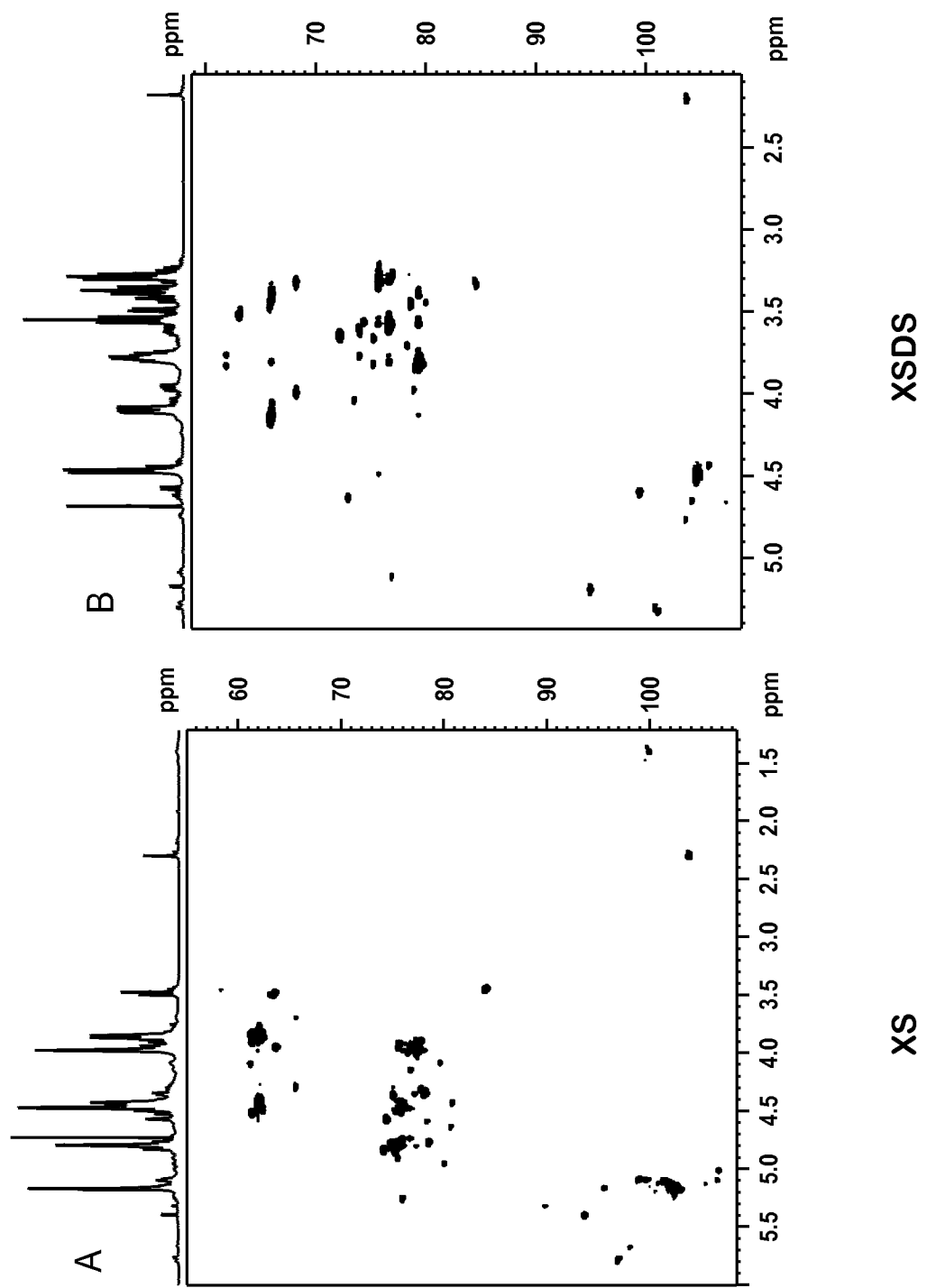

The NMR spectrum of Heteronuclear Single Quantum Coherence (HSQC) of samples of pentosan polysulfate shows a series of signals corresponding to the different positions of the units of xylose and 4-O-methyl-glucuronic acid of the polysaccharide (FIG. 2-A).

The attribution of each detected signals to specific chemically defined positions is made difficult by the large number of structural combinations similar to each other present in the polysaccharide, and therefore by the presence of a multitude of signals in the HSQC NMR spectrum; these signals are close each other in the spectrum and partially overlapped. The multiplicity of positions chemically similar, but spectroscopically distinguishable derives from the combination of the various possible patterns of substitution with functional groups (sulfate, hydrogen or acetyl) or ramifications of the xylose unit of the chain, reducing end or non-reducing end. The signals corresponding to the units of 4-O-methyl-glucuronic acid which are present in the various possible structural variety overlap to the signals corresponding to the above reported species.

This situation hampers the work of attribution of all the HSQC NMR signals to specific structural contexts.

By repeating the NMR experiment on samples of pentosan polysulfate for pharmaceutical use that had been subjected to a procedure of exhaustive desulfation to obtain the corresponding xylan without sulfate groups, a higher resolution of the signals and the simplification of the HSQC spectrum was found. The chemical environments corresponding to the different positions of the polysaccharide are apparently more differentiated each other in the desulfated product than in the sulfated product. In addition, the removal of the sulfate groups reduces the structural variability of the different constituent units of the polysaccharide taking into consideration that also in pentosan polysulfate, notwithstanding its high sulfation degree, not completely sulfated saccharide units are present and that each of these can be associated with a series of NMR signals.

Therefore a reduction of the structural variety corresponds to a simplification of the NMR spectrum (FIG. 2-B)

Therefore it was possible, by combining several NMR techniques such as analysis HSQC, HMBC, TOCSY and COSY, to find that the acetyl group is not equally distributed between the positions 2 and 3 of the repeating units which constitute pentosan polysulfate, but it is mainly present at position 3 of the repeating units of xylose.

Furthermore the Applicant found that said acetyl groups are mainly bound to the position 3 of the xylose units which have also a 4-O-methyl-glucuronic acid unit in position 2.

The Applicant has therefore determined experimentally that pentosan polysulfate for pharmaceutical use is characterized by the presence of units of xylose substituted with 4-O-methyl-glucuronic acid and acetylated which represent structural characteristic units.

Figure 3:
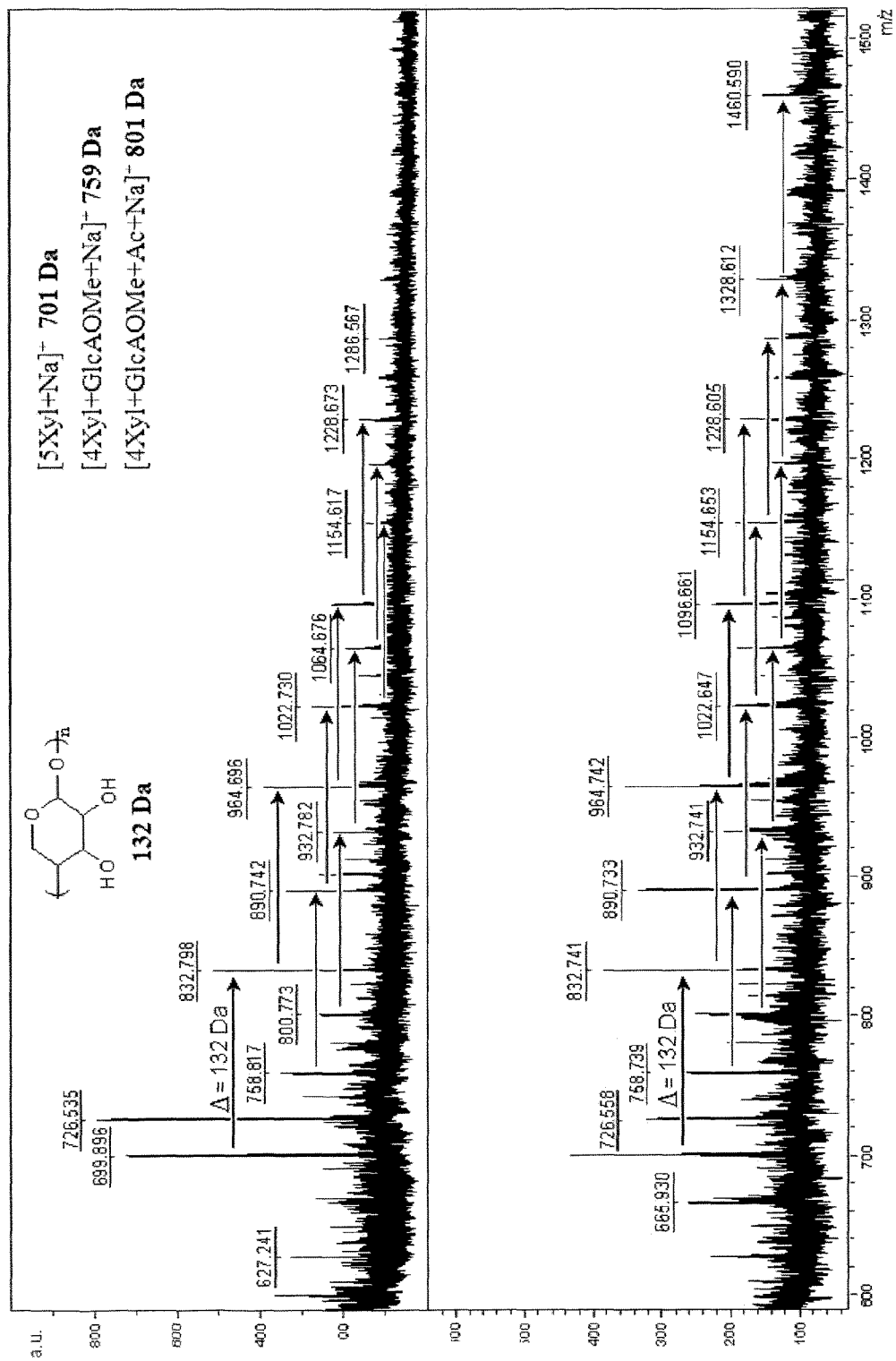

This determination of the structural units of the polysaccharide has been confirmed by the mass spectroscopy analysis of the xylan obtained by exhaustive desulfation of pentosan polysulfate on which a Maldi TOF analysis was carried out. FIG. 3 shows the resultant spectrum showing the presence of three different sets of sequences that differ by the value corresponding to the mass of the repeating unit of xylose (132 daltons), having the following masses:

the first series having peaks with mass of 701, 833, 965, 1165 Da, etc. corresponding to oligomers of polyxylan (Xyl)n the second series having peaks with mass of 759, 891, 1023, 1155 Da, etc. corresponding to oligomers of polyxylan with a branch of 4-O-methyl-glucuronic acid (Xyl)n-(Xyl-GlcAOMe)-(Xyl)m the third series having peaks with mass of 801, 933, 1065 Da, etc. corresponding to oligomers of polyxylan with a branch of 4-O-methyl-glucuronic acid in which an acetyl group is also present (Xyl)n-(Xyl-OAc-GlcAOMe)-(Xyl)m The results obtained from the characterization by MALDI TOF mass spectroscopy show that the acetyl group is bound to the structure of the polysaccharide. Said results also show that the acetyl group is mainly present in species in which there is also a 4-O-methyl-glucuronic acid group. By suitably combining the results of the NMR analysis it was possible to fill in the following Table 1 with the assignment of the NMR signals relative to the sample obtained by desulfation procedure.

TABLE 1

| Position | Saccharide | Type | $^1$H ppm | $^{13}$C ppm |
|---|---|---|---|---|
| 1 | Xyl | internal | 4.47 | 104.61 |
|   | Xyl | nr | 4.44 | 104.87 |
|   | Xyl | redα | 5.17 | 94.98 |
|   | Xyl | redβ | 4.57 | 99.47 |
|   | Xyl | having 4-MGA bound in 2 | 4.74 | 103.61 |
|   | Xyl | acetylated in 3 + 4-MGA bound in 2 | 4.63 | 104.17 |
|   | 4-MGA | bound to Xyl | 5.27 | 100.88 |
|   | 4-MGA | bound to Xyl acetylated in 3 | 5.30 | 101.16 |
| 2 | Xyl | internal | 3.29 | 75.69 |
|   | Xyl | nr | 3.29 | 75.69 |
|   | Xyl | redα | 3.53 | 74.39 |
|   | Xyl | redβ | 3.24 | 77.00 |
|   | Xyl | having 4-MGA bound in 2 | | |
|   | Xyl | acetylated in 3 + 4-MGA bound in 2 | 3.68 | 78.41 |
|   | 4-MGA | bound to Xyl | 3.58 | 73.93 |
|   | 4-MGA | bound to Xyl acetylated in 3 | 3.58 | 73.93 |
| 3 | Xyl | internal | 3.55 | 76.68 |
|   | Xyl | nr | 3.42 | 78.66 |
|   | Xyl | redα | 3.75 | 74.00 |
|   | Xyl | redβ | 3.55 | 76.68 |
|   | Xyl | having 4-MGA bound in 2 | | |
|   | Xyl | acetylated in 3 + 4-MGA bound in 2 | 5.09 | 76.99 |
|   | 4-MGA | bound to Xyl | 3.65 | 75.21 |
|   | 4-MGA | bound to Xyl acetylated in 3 | 3.80 | 75.22 |
| 4 | Xyl | internal | 3.78 | 79.36 |
|   | Xyl | nr | 3.62 | 72.22 |
|   | Xyl | redα | 3.78 | 79.36 |
|   | Xyl | redβ | 3.78 | 79.36 |
|   | Xyl | having 4-MGA bound in 2 | 3.78 | 79.36 |
|   | Xyl | acetylated in 3 + 4-MGA bound in 2 | 3.94 | 78.87 |
|   | 4-MGA | bound to Xyl | 3.80 | 84.31 |
|   | 4-MGA | bound to Xyl acetylated in 3 | 3.82 | 84.46 |

TABLE 1-continued

| Position | Saccharide | Type | $^1$H ppm | $^{13}$C ppm |
|---|---|---|---|---|
| 5 | Xyl | internal | 4.10 | 65.96 |
|  | Xyl | nr | 3.96 | 68.21 |
|  | Xyl | redα | 3.81 | 61.86 |
|  | Xyl | redβ | 4.10 | 65.96 |
|  | Xyl | having 4-MGA bound in 2 | 4.10 | 65.96 |
|  | Xyl | acetylated in 3 + 4-MGA bound in 2 | 4.10 | 65.96 |
|  | 4-MGA | bound to Xyl | 4.03 | 73.22 |
|  | 4-MGA | bound to Xyl acetylated in 3 | 4.64 | 72.67 |
| 5' | Xyl | internal | 3.37 | 65.95 |
|  | Xyl | nr | 3.30 | 68.21 |
|  | Xyl | redα | 3.74 | 61.86 |
|  | Xyl | redβ | 3.37 | 65.95 |
|  | Xyl | having 4-MGA bound in 2 | 3.37 | 65.95 |
|  | Xyl | acetylated in 3 + 4-MGA bound in 2 | 3.37 | 65.95 |
| Others | 4-MGA | O—CH$_3$ bound to Xyl | 3.49 | 63.00 |
|  | 4-MGA | O—CH$_3$ bound to Xyl acetylated in 3 | 3.49 | 63.00 |
|  | 4-MGA | —COOH MGA bound to Xyl |  | 176.50 |
|  | 4-MGA | —COOH MGA bound to Xyl acetylated in 3 |  | 177.00 |
|  | Xyl | O-Ac (methyl) | 2.17 | 23.89 |
|  | Xyl | O-Ac (carbonyl) |  | 176.60 |
|  |  | TSP | 0 |  |

Xyl—xylose
4-MGA—4-O-methyl-glucuronic
TSP—trimethylsilylpropionate
Ac—acetyl
nr—saccharide unit at the non-reducing end
redα—saccharide unit at the reducing end α
redβ—saccharide unit at the reducing end β

By using the information collected from the analysis of samples of xylan obtained by desulfation of pentosan polysulfate it was possible to complete the assignment of the NMR signals for the not desulfated product. Combining this information with the results of the NMR experiments, such as HSQC, HMBC, TOCSY and COSY, carried out directly on not desulfated samples the results of the structural analysis were confirmed and the following table 2 has been prepared on the basis of the $^1$H and $^{13}$C NMR signals of pentosan polysulfate.

TABLE 2

| Position | Saccharide | Type | $^1$H ppm | $^{13}$C ppm |
|---|---|---|---|---|
| 1 | Xyl(S) | internal | 5.17 | 102.40 |
|  | Xyl(S) | nr | 5.17 | 102.40 |
|  | Xyl(S) | redα | 5.39 | 93.68 |
|  | Xyl(S) | redβ | 5.10 | 101.38 |
|  | Xyl(S) | having 4-MGA(S) bound to 2 |  |  |
|  | Xyl(S) | acetylated in 3 + 4-MGA(S) bound to 2 | 5.00 | 106.73 |
|  | 4-MGA(S) | bound to Xyl(S) | 5.79 | 96.86 |
|  | 4-MGA(S) | bound to Xyl(S) acetylated in 3 | 5.76 | 96.99 |
| 2 | Xyl(S) | internal | 4.47 | 75.85 |
|  | Xyl(S) | nr | 4.49 | 75.39 |
|  | Xyl(S) | redα | 4.35 | 78.16 |
|  | Xyl(S) | redβ | 4.42 | 75.88 |
|  | Xyl(S) | having 4-MGA(S) bound to 2 |  |  |
|  | Xyl(S) | acetylated in 3 + 4-MGA(S) bound to 2 | 3.93 | 76.85 |
|  | 4-MGA(S) | bound to Xyl(S) | 4.32 | 78.22 |
|  | 4-MGA(S) | bound to Xyl(S) acetylated in 3 | 4.31 | 77.76 |
| 3 | Xyl(S) | internal | 4.80 | 75.36 |
|  | Xyl(S) | nr | 4.83 | 74.20 |
|  | Xyl(S) | redα | 4.76 | 78.55 |
|  | Xyl(S) | redβ | 4.74 | 75.99 |
|  | Xyl(S) | having 4-MGA(S) bound to 2 |  |  |
|  | Xyl(S) | acetylated in 3 + 4-MGA(S) bound to 2 | 5.25 | 75.96 |
|  | 4-MGA(S) | bound to Xyl(S) | 4.95 | 80.04 |
|  | 4-MGA(S) | bound to Xyl(S) acetylated in 3 | 4.42 | 80.83 |
| 4 | Xyl(S) | internal | 3.97 | 77.38 |
|  | Xyl(S) | nr | 4.57 | 74.40 |
|  | Xyl(S) | redα | 3.89 | 77.78 |
|  | Xyl(S) | redβ | 3.97 | 76.70 |
|  | Xyl(S) | having 4-MGA(S) bound to 2 |  |  |
|  | Xyl(S) | acetylated in 3 + 4-MGA(S) bound to 2 | 4.14 | 76.79 |
|  | 4-MGA(S) | bound to Xyl(S) | 3.45 | 84.04 |
|  | 4-MGA(S) | bound to Xyl(S) acetylated in 3 | 3.45 | 84.04 |
| 5 | Xyl(S) | internal | 4.44 | 61.92 |
|  | Xyl(S) | nr | 4.51 | 61.40 |
|  | Xyl(S) | redα | 3.94 | 63.69 |
|  | Xyl(S) | redβ | 4.44 | 61.92 |
|  | Xyl(S) | having 4-MGA(S) bound to 2 |  |  |
|  | Xyl(S) | acetylated in 3 + 4-MGA(S) bound to 2 | 4.29 | 65.60 |
|  | 4-MGA(S) | bound to Xyl(S) | 4.36 | 75.05 |
|  | 4-MGA(S) | bound to Xyl(S) acetylated in 3 | 3.92 | 75.71 |
| 5' | Xyl(S) | internal | 3.86 | 61.92 |
|  | Xyl(S) | nr | 3.89 | 61.40 |
|  | Xyl(S) | redα | 3.94 | 63.64 |
|  | Xyl(S) | redβ | 3.86 | 61.92 |
|  | Xyl(S) | having 4-MGA(S) bound to 2 |  |  |
|  | Xyl(S) | acetylated in 3 + 4-MGA(S) bound to 2 | 3.69 | 65.60 |
| Others | 4-MGA(S) | O—CH$_3$ bound to Xyl(S) | 3.50 | 63.37 |
|  | 4-MGA(S) | O—CH$_3$ bound to Xyl(S) acetylated in 3 | 3.48 | 63.61 |
|  | 4-MGA(S) | —COOH 4-MGA(S) bound to Xyl(S) |  | 178.90 |
|  | 4-MGA(S) | —COOH 4-MGA(S) bound to Xyl(S) acetylated in 3 |  | 178.44 |
|  | Xyl(S) | O-Ac (methyl) | 2.30 | 23.37 |
|  | Xyl(S) | O-Ac (carbonyl) |  | 176.14 |

Xyl(S)—xylose sulfate
4-MGA(S)—4-O-methyl-glucuronic sulfate
Ac—acetyl
nr—saccharide unit at the non-reducing end
redα—saccharide unit at the reducing end α
redβ—saccharide unit at the reducing end β

Based on the obtained results, the Applicant has attributed to pentosan polysulfate for pharmaceutical use the structure of formula 2:

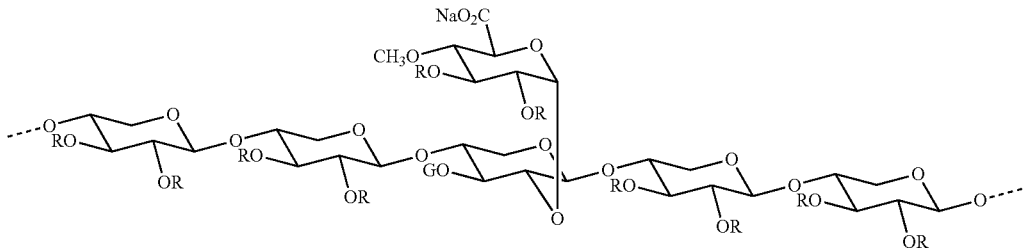

Formula 2 wherein
R is H or SO₃Na
G is H, SO₃Na or acetyl;
wherein the structural group G which can be an acetyl group, is present.

The Applicant has then experimentally defined that pentosan polysulfate for pharmaceutical use is characterized by the presence of xylose units substituted by 4-O-methyl-glucuronic acid and acetylated (G=acetyl) as characteristic structural units.

This high structural specificity is a characterizing feature of pentosan polysulfate used as active pharmaceutical ingredient for human use.

The identification of this specific structural unit of pentosan polysulfate has several useful applications such as the selection of the method of isolation of the raw material (xylan from beech), the evaluation of the process for the transformation of xylan into the final product comprising the steps of depolymerization and sulfation, the procedures for the isolation and purification of the resultant pentosan polysulfate, the evaluation of batches of the production of intermediates and final product.

The above features has a further practical application of the invention consisting in the xylan obtained by the desulfation of pentosan polysulfate or by other methods and represented by formula 2 wherein R is hydrogen and G is hydrogen or acetyl as well as in the use of said xylan as raw material for the preparation of pentosan polysulfate for pharmaceutical use by preserving its structural units.

A further practical embodiment of the present invention is the possibility to make more meaningful the process controls at different production steps by linking them to specific structural parameters.

These factors will be taken into account in the production and marketing of pentosan polysulfate for pharmaceutical use and should also be considered as part of the registration process of the product before the regulatory authorities, such as the FDA, for the authorization of generic versions of pentosan polysulfate.

These assessments are not limited to the check of the presence of the characteristic structural unit, but also to its quantification. For this purpose, NMR spectroscopy may still be used. Through this technique we have found that the presence of the acetyl groups is mainly in the position 3 of the repetitive xylose units. In addition we have found that said acetyl groups are mainly bound to the position 3 of xylose units also having a 4-O-methyl-glucuronic acid unit bound in position 2. By integration in the HSQC spectrum of different samples of xylan and pentosan polysulfate, the amount of xylose units having both an acetyl group and a 4-O-methyl-glucuronic acid unit was determined (determined by integrating the signal relative to the position 3 of the specified xylose unit), with respect to the total xylose units bearing a 4-O-methyl-glucuronic acid unit in position 2 (integrating the corresponding signals of the positions 1). Based on the obtained data, the Applicant has been able to determine that the content of xylose units substituted with 4-O-methyl-glucuronic acid which also have an acetyl group in the pentosan polysulfate for pharmaceutical use and in the corresponding xylan without sulfate groups is at least 20%, preferably between 35% and 70%, with respect to the total amount of the present residues of 4-O-methyl-glucuronic acid.

Therefore, preferred features of the present invention are xylan and pentosan polysulfate of formula 2 containing at least 20% of xylose units substituted with a 4-O-methyl-glucuronic acid that are acetylated as characteristic structural units obtained with a method that comprises at least one qualification step based on said characteristic structural units.

In further particularly preferred aspects the present invention relates to xylan and pentosan polysulfate of formula 2 containing between 35% and 70% of xylose units substituted with a 4-O-methyl-glucuronic acid that are acetylated as characteristic structural units obtained with a method that comprises at least one qualification step based on said characteristic structural units.

This quantitative evaluation involves multiple advantages such as the selection of the method of isolation of the raw material (xylan from beech), the evaluation of the transformation process of xylan into the final product comprising the steps of depolymerization and sulfation, the isolation and purification procedures of the resultant pentosan polysulfate, the assessment of production batches of raw material, intermediate and final product.

Then, also these structural features related to the quantification of the structural unit will be taken into account for the production and marketing of pentosan polysulfate for pharmaceutical use; furthermore these structural features also have to be considered as part of the registration process of the product before the regulatory authorities, such as for example the FDA, for the authorization of generic versions of pentosan polysulfate.

The identification of the characteristic structural units of xylan and pentosan polysulfate was carried out as previously described by using advanced spectroscopic techniques, however, the methods of the present invention are not limited to these techniques, but also include the use of the information relating to the presence and quantification of such characteristic structural unit determined by any analytical technique such as IR spectroscopy, HPLC analysis, analysis of the products of depolymerization, ELISA, capillary electrophoresis.

The absence or the presence and the quantification of the signals of the characteristic structural unit are determined by any method that allows the identification in the preparation of xylan or xylan sulfate as such, their fractions or their hydrolysis products. For example, one or more of the following methods may be used: nuclear magnetic resonance (NMR), mass spectrometry, for example matrix-assisted laser desorption ionization mass spectrometry (MALDI-MS), electrospray ionization mass spectrometry (ESI MS), coupled or not to chromatographic separation techniques (for example size exclusion, ionic, etc.).

The methods of the present invention preferably use NMR spectroscopy, even more preferably the HSQC NMR spectroscopy.

The use of the information relating to the presence and the quantification of the characteristic structural units for the qualification and the selection of batches of pharmaceutical pentosan polysulfate active ingredient is of particular importance. In that case, on the basis of this information the decision whether to approve, reject, or possibly rework batches of pentosan polysulfate for pharmaceutical use may be taken.

In order to better illustrate the present invention without limiting it, the following examples are now given.

Example 1

Procedure for the Desulfation of Pentosan Polysulfate 500 mg of pentosan polysulfate (Elmiron®) were converted into the acid form by treatment with an ion exchange resin (Amberlite IR 120 H+) and the resultant solution (50 mL) was neutralized with pyridine and then lyophilized. The pyridine salt was dissolved in a solution of DMSO (2 mL) containing 10% of $H_2O$ and the solution was heated at 80° C. for 4 hours. After this time the solution was added to a volume of water at least 3 times higher and cooled. The xylan sample without sulfate groups was isolated after suitable purification operations (precipitation, dialysis, Size Exclusion Chromatography). This procedure was repeated to prepare at least 3 samples (P5146, P5211 and P5212).

Example 2

Procedure for the Recordal of NMR Spectra

The spectra were recorded with a spectrometer Bruker AVANCE 500 or 600 MHz equipped with a cryoprobe.

Sample preparation: about 20 mg were dissolved in 0.6 mL of $D_2O$ (99.9% deuterated water D) or in a mixture $D_2O$/DMSO (deuterated dimethyl sulfoxide) in 1:9 ratio and transferred into a tube for NMR analysis of 5 mm. The $^1$H-NMR spectra were acquired at a temperature of 303 Kelvin with pre-saturation of the water signal with an interval of recycle of 12 s, for a number of scans from 16 to 24 calibrating the spectrum with respect to TSP.

Example 3

Identification of Characteristic Parameters of the Structure of Pentosan Polysulfate or Xylan without Sulfate Groups Via Two-Dimensional (2D) NMR The 2D NMR experiments can be homonuclear (for example COSY, TOCSY, etc.) or heteronuclear (HSQC, HSQC-DEP, HMQC, HMBC, etc.). All the 2D spectra (HSQC, HMBC, COSY, TOCSY and HSQC-TOCSY) were carried out on samples prepared under the same conditions described for the $^1$H-NMR spectrum and acquired at a temperature of 303 Kelvin, calibrating the spectrum with respect to TSP if performed in $D_2O$ solvent and with respect to the peak of DMSO solvent, if the spectra were carried out in DMSO/$D_2O$ solvent.

Two-dimensional spectra DQF (double-quantum-filter)-COSY and 2D-TOCSY were acquired using from 16 to 24 scans per set of 2048×512 data points with zero filling in F1 (4096×2048), a function "shifted ($\pi/3$) squared cosine" was applied before the Fourier transform. The spectrum HSQC (heteronuclear single-quantum coherence) was obtained in "phase sensitivity enhanced pure-absorption mode" with decoupling during acquisition. The dimensions of the matrix were of 1024×320 data points that were "zero-filled" at 4096×2048 by applying a cosine square function before the Fourier transform.

A HMBC experiment on a xylan sample without sulfate groups showed a long range correlation between the signal of the residue of xylose and a carboxyl group of the acetyl group.

This signal was identified through an experiment COSY and HSQC-TOCSY as the position 3 of a xylose residue carrying the acetyl group. The position 2 of said residue was found to correlate in the HMBC spectrum with a residue of glucuronic acid highlighting the presence of glucuronic acid in the position 2 and of the acetyl group in position 3 of the same xylose residue. This explained the splitting of the signals relating to the glucuronic acid residue in positions 1, 3, 4 and 5 in addition to the splitting of the signal of the 0-Me group.

The two-dimensional experiments described above allowed also to identify the chemical shifts of the reducing/non-reducing residues and the characteristic parameters of the structure as shown in Table 1. The HMBC experiment on the sample of Elmiron® (pentosan polysulfate) showed similar long-range correlations between the signal corresponding to the position 3 of the acetylated xylose residue and the carboxyl group of the acetyl group. The two-dimensional spectra also allowed the assignment of the signals reported in Table 2.

Example 4

Quantification of Characteristic Parameters of the Structure of Xylan without Sulfate Groups and Pentosan Polysulfate The absence or the presence and the quantification of the signals of the characteristic structural units were determined with 2D-NMR spectra of xylans without sulfate groups obtained by desulfation as described in example 1 and with the spectra of pentosan polysulfate and were associated with the presence of a signal in the region corresponding to residues of xylose bearing the acetyl group. It resulted that the acetyl group was not distributed in an equivalent manner between the positions 2 and 3 of the repetitive units forming the polysaccharide structure, but was mainly concentrated in the position 3 of the repetitive xilose units.

It also resulted that these acetyl groups were mainly bound to the position 3 of xylose units bearing also a 4-O-methyl-glucuronic acid unit in position 2. The presence of the signal meant that the characteristic structural unit can be detected and quantified by integration as % in comparison with the total number of present residues of 4-O-methyl-glucuronic acid.

The following table 3 reports the values of the quantification carried out on different samples.

TABLE 3

| | Pentosan polysulfate Elmiron ® samples | | | Xylan samples without sulfate groups obtained by desulfation of pentosan polysulfate Elmiron ® | | |
| --- | --- | --- | --- | --- | --- | --- |
| | P5093 | P5196 | P5197 | P5146 | P5211 | P5212 |
| Xylose units substituted with 4-O-methyl-glucuronic acid that are bearing also the acetyl group (% Ac) | 60.5% | 54.5% | 44.0% | 58.8% | 46.0% | 37.5% |

The quantification of the percentage of the xylose units substituted with 4-O-methyl-glucuronic acid that are bearing also the acetyl group (% Ac) was calculated by processing the integrals of the NMR signals according to the formula:

% Ac=∫C3-XylAc/∫ΣC1-Glc wherein:
∫C3-XylAc=integral of the signal of the position 3 of the xylose bearing the acetyl group in 3 and the 4-O-methyl-glucuronic acid in 2
∫ΣC1-Glc=integral of the sum of the signals of the position C1 of 4-O-methyl-glucuronic acid, bound to xylose with acetyl group and bound to xylose without acetyl group.

The analysis was also carried out on a sample of pentosan polysulfate for pharmaceutical use from a different manufacturer and bought on the Indian market. The signals of OAc group at 2.3 ppm, of C3-XylAc group at 5.25/75.96 ppm and of C1-XylAc group at 5.00/106.73 ppm were not detected in its NMR spectra.

The NMR analysis of this sample showed the presence of structures which are not present in pentosan sulfates extracted from the commercial product Elmiron®, associated with signals in different regions of the spectrum, and in particular between 5.8/6.2 ppm and 95/115 ppm, highlighting the diagnostic capability of this technique for structural investigation.

Example 5

Mass Analysis of Xylan

The mass spectrometry was applied as an orthogonal technique of structural analysis. The xylan sample without sulfate groups obtained as described in example 1 was analyzed via MALDI mass spectrometry following the procedure below. The sample was dissolved in $H_2O$ at a concentration of approximately 0.5 mg/mL. 1 microliter of the analyte solution was added to 5 microliters of a solution of DHB matrix at a concentration of 10 mg/mL in 80% EtOH. 1 microliter of the mixture was placed on the target and analyzed with a spectrometer Bruker Daltonics Autoflex MALDI TOF in positive polarity and in reflectron mode.

The invention claimed is:
1. An O-acetyl-(4-O-methylglucurono)-xylan polysaccharide wherein between about 35% to about 60% of the xylose units substituted with 4-O-methyl-glucuronic acid also bear an acetyl group.
2. A polysaccharide according to claim 1 wherein about 70% of all acetyl groups are bound to the position 3 of the xylose units also having the 4-O-methyl-glucuronic acid unit bound in position 2.

* * * * *